(12) United States Patent
Kahol et al.

(10) Patent No.: US 6,309,678 B1
(45) Date of Patent: Oct. 30, 2001

(54) **PROCESS FOR ISOLATION OF HEPATOPROTECTIVE AGENT SILYMARIN FROM THE SEEDS OF THE PLANT *SILYBUM MARIANUM***

(75) Inventors: Atul Prakash Kahol; Kiran Lata Singh; Sudeep Tandon; Sushil Kumar, all of Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/541,035

(22) Filed: Mar. 31, 2000

(51) Int. Cl.[7] .................... A01N 65/00; A61K 35/78; A61K 39/385
(52) U.S. Cl. .................................. 424/776; 424/725
(58) Field of Search ........................ 424/195.1, 776, 424/725

(56) References Cited

U.S. PATENT DOCUMENTS 5,955,084 * 9/1999 Jain et al. ........................ 424/195.1

FOREIGN PATENT DOCUMENTS

2084569 A * 4/1982 (GB) ................... C07D/407/04

1975-39334W * 4/1975 (WO) ................... C07D/21/00

* cited by examiner

*Primary Examiner*—Jean C. Witz
*Assistant Examiner*—Brett Ozga
(74) *Attorney, Agent, or Firm*—Wenderoth, Lind & Ponack, L.L.P.

(57) ABSTRACT

The invention relates to a novel process for the isolation of a hepatoprotective agent Silymarin from the seeds of the plant *Silybum marianum* comprising (i) Precooling the seeds to (−) 20° C. for 24 hours in a deep freezer/cold room. (ii) Powdering the cooled seeds in a hammer mill, fitted with about 40 mesh discharge screen. (iii) Defatting the seeds by extracting with hexane in a soxhlet type extractor to remove the total quantity of fatty oil without using a scrain. (iv) Extracting the defatted seeds with acetonitrile at 20–30° C. to extract silymarin fraction. (v) Concentration of the sensitive silymarin fraction under vacuum in a agitated wiped thin film evaporator (vi) stirring the silymarin such dry powder with cold dichloromethane at 5° C. followed by filtration and drying with a slow purge of nitrogen gas. (vii) Further purification of silymarin by suspending in 5 times its weight of acetonitrile and precipitating by 8–12 times its weight of water at 20° C. (viii) Filtering the precipitated silymarin in a closed vacuum filter and having 1–2 μm screen washing the cake three times with distilled water (ix) Drying of Silymarin cake in vacuum oven to obtain substantially pure silymarin.

12 Claims, No Drawings

US 6,309,678 B1

PROCESS FOR ISOLATION OF HEPATOPROTECTIVE AGENT SILYMARIN FROM THE SEEDS OF THE PLANT *SILYBUM MARIANUM*

FIELD OF THE INVENTION

The invention relates to a novel process for the isolation of a hepatoprotective agent silymarin from the plant *Silybum marianum* (L) Gaertn.

1. Background of the Invention

Silymarin is the name given to a mixture of flavanolignans found in *Silybum marianum* which have exhibited clinically proven hepatoprotective action. Positive results obtained in numerous pharmacological, biochemical and toxicological studies have made silymarin a drug of choice in the treatment of diseases of the liver (Morazzoni, P. and Bombardelli, E., *Fitoterapia*, 116(1), p 1005, 1995). Major constituents of silymarin have been identified as the flavanolignans silybin, silydianin and silychristin and their chemical structures have been elucidated (Wagner, H., Diesel, P., and Seitz, M., Arzneim Forsch. 24, p 466, 1974; Pelter, A., Hansel, R., *Tetrahedron Letters*, No.25, p 2911–2916, 1968; Abraham D J, Takagi S, Wagner H, Farnsworth N R, et al, *Tetrahedron Letters*, No.31, p. 2675–2678, 1970; Wagner H, Cahri, M. V, Seitz M; Riess-Muarer, I, *Tertrahedron Letters*, No.4, p 381–384, 1978). The mechanism of hepatoprotective action of silymarin has been attributed to its ability to act as a powerful scavenger of free radicals capable of interrupting the peroxidative processes involved in liver damage induced by hepatotoxic agents like alcohol, paracetamol and carbon tetrachloride (Leng, P. E., Strange, H. A., Z. Phytotherapie 12, 162, 1991). Considering the widespread use of alcohol causing liver problems in humans and the general prevalence of liver diseases caused by impure drinking water, the demand for silymarin is huge. Silymarin is extracted from the mature dry seeds of *Silybum marianum*. A few methods for isolation of silymarin have been reported.

2. Prior Art References

According to one process, the powdered drug was extracted in soxhlet extractor with methanol or ethanol, the extract, concentrated under reduced pressure, concentrate made into a slurry with silica gel and loaded onto a silica gel column, eluted with benzene-ethyl acetate mixtures of increasing polarity, silymarin containing fractions combined and solvent removed, residue crystallized from MeOH gave 86% pure silybin (mp 167° C.–180° C.), mother liquor completely dried under vacuum gave additional yellow mixture of flavanoids having 58% purity as silybin (Gupta, G. K., Raj, S., Rao, P. R., *Research and Industry* 27, p 37–42, 1982). The highest yield of Silymarin reported by these authors was 2.46% based on the weight of seeds. This process involves the costly step of silica gel chromatography which is not economical when used on industrial scale. Another process presently being used consists of removing part of the fatty oil by pressing the seeds in a screw press, breaking up the compressed seed mass, extracting the pressed seed mass with ethyl acetate at 75° C., evaporating the solvent to obtain a semisolid residue, defatting the residue by repeated solid liquid extraction with light petroleum, dissolving defatted residue in methanol, mixing methanol solution with chloroform and water, separating and retaining methanolic layer, evaporating aqueous methanol, suspending residue in a little methanol, precipitating the silymarin rich solid by mixing with excess water, centrifuging, washing and drying the precipitate in vacuo. Yield of Silymarin is 1.7% based on dry seed weight. (Madaus, R. Klaus, G., Werner, M., U.S. Pat. No. 4,368,195 Jan. 11, 1983).

OBJECT OF THE INVENTION

The main objective of the present invention is to provide a simple process to isolate the hepatoprotective agent silymarin from the seeds of *Silybum marianum*.

Another object is to provide a novel, cheap and economic process for isolation of silymarin on commercial scale.

SUMMARY OF THE INVENTION

Accordingly, the invention provides a novel process for the isolation of Silymarin, a hepatoprotective agent, from the seeds of *Silybum marianum*.

DETAILED DESCRIPTION

Accordingly, the invention provides a novel process for the isolation of Silymarin, a hepatoprotective agent, from the seeds of *Silybum marianum*, said process comprising the steps of:

i) chilling the seeds of *Silybum marianum*,
ii) grinding the chilled seeds to a fine powder,
iii) defatting the pulverized seeds by extracting it with a hydrocarbon solvent,
iv) extracting the defatted seed powder with acetonitrile at 20–30° C. to obtain silymarin-containing fraction as an extract,
v) concentration of the sensitive silymarin fraction,
vi) stirring the silymarin rich dry powder with cold dichloromethane at 5° C. followed by filtration and drying with a slow purge of nitrogen gas,
vii) purification of silymarin by suspending it in acetonitrile in an amount 5 times its weight and precipitating it by adding distilled water in an amount 8–12 times its weight, at 20–30° C.,
viii) filtering the precipitated silymarin in a closed vacuum filter having 1 to 2 $\mu$m screw, washing the cake three times with distilled water, and
ix) drying the silymarin cake in vacuum oven to obtain substantially pure silymarin.

In an embodiment, the seeds of the plant *Silybum marianum* are cooled for 24 hrs. at −20° C. in a deep freezer or cold room.

In an embodiment, the hydrocarbon solvent for removal of fatty acids is hexane.

In an embodiment, the chilled seeds are pulverized in a hammer mill fitted with about 40 mesh discharge screen.

Still another embodiment, the fatty oil in the seed powder is removed by extraction in a soxhlet type extractor without using screw/press.

In yet another embodiment, the extract containing sensitive silymarin obtained in step (iv) is concentrated using an agitated wiped thin film evaporator.

In yet another embodiment. In another embodiment of invention the filtration of the silymarin containing fractions is carried out in closed vacuum filter under the inert environment of nitrogen gas to prevent the degradation of the product.

In still another embodiment the silymarin precipitate is dried under vacuum at 40–45° C., maintaining oven pressure at 5–15 torr for 15 hours.

The invention is described in detail herein below with reference to the following examples which are provided merely to illustrate the invention and should not be construed to limit the scope of the invention in any manner.

Primarily, the improved process consists of following operations

1. Chilling the seeds of *Silybum marianum* at (−)20° C. by keeping overnight in a deep freezer/cold room.
2. Grinding the chilled seeds in a hammer mill fitted with 40 mesh discharge screen.
3. Extracting the powdered seeds in a soxhlet apparatus with a hydrocarbon solvent such as hexane to remove all the fatty oil.
4. Percolating the defatted seed powder 34 times with acetonitrile at (20° C.–30° C.) for separating the silymarin containing fraction, as extract.
5. Removing the acetonitrile under vacuum in a wiped film evaporator to obtain a concentrate rich in silymarin, recovered acetonitrile being recycled to the process.
6. Drying the concentrate in a batch type stirred vacuum concentrator to obtain a product of semi solid consistency and its further drying in a vacuum oven to obtain a dry residue.
7. Stirring the powdered residue in cold dichloromethane (5° C.) and filtering in a closed vacuum filter for removing the impurities from silymarin rich solid product.
8. Dissolving the above solid in small amount of acetonitrile and precipitating silymarin by adding cold distilled water.
9. Filtering the light yellow precipitate and washing it three times with distilled water.
10. Transferring the cake to a vacuum oven and drying it at 40–45° C., maintaining the oven pressure at 5–15 torr for 15 hours.
11. Checking the purity of product obtained by DNPH method using a UV spectrophotometer at 490 nm (Wagner, V. H., Diesel, P., Saity, M., Ahzneim.—Forsch, 24 (4), p 466–471, 1974) and by HPLC (Tittel and Wagner, *Journal of Chromatography*, 153, p 227–232, 1978).

Salient Features of the Invention

1. The prior art process depends on a screw press to remove part of fatty oil present in the seeds. The remaining oil is removed in a second step of solid-liquid extraction done with light petroleum on the crude extract obtained from ethyl acetate extraction of the seeds at 75° C. which follows the screw press operation. This invention achieves complete removal of fatty oil in a single step by soxhlet extraction with hexane of a carefully prepared crushed seed mass. The step of chilling the seeds to (−) 20° C. prior to crushing in a hammer mill fitted with a 40 mesh discharge screen is particularly ingenious as it makes the seeds brittle and friable. Choice of a hammer mill fitted with a 40 mesh discharge screen is particularly ingenious as it makes the seeds brittle and friable. Choice of a hammer mill fitted with the particular screen is appropriate as it affords a powdered seed mass amendable to efficient percolation with solvent which achieves complete removal of fatty oil in just 3 washes. Unlike the prior art process no mechanical stirring is required in this invention which simplifies the operation and saves energy cost. Extraction of fatty oil with screw press as in the prior art process also has the problem of fine seed particles going into the oil which then has to be filtered to recover the seed material, balance amount of oil has to be recovered in a solid-liquid extraction step carried out on the ethyl acetate extract. The process of this invention is much simpler and efficient to remove total quantity of fatty oil in a single step and saving valuable process time.
2. The prior art process involves extraction of defatted seed with hot ethyl acetate at 75° C. and filtration of hot slurry to obtain the extract. This invention has selected acetonitrile to more selectively separate the silymarin containing fraction from the defatted seed mass at 20° C. to 30° C. Process advantage is gained in two areas by operating at room temperature as compared to 75° C. as in prior art process; (a) filtration of hot ethyl acetate containing slurry at 75° C. (b.p. Ethyl acetate= 77° C.) is likely to emit toxic solvent fumes unless special enclosures are designed, (b) The process of this invention by operating near room temperature is simpler and less hazardous to working environment.
3. The prior art processes involves the concentration of the silymarin rich extract by prolonged distillation/evaporation at 50° C. Considering the sensitive nature of flavolignans molecules which constitute Silymarin, the process of this invention employs an agitated wiped thin film evaporator under vacuum to carry out the concentration of silymarin containing extracts. Evaporators of agitated wiped thin film design have the ability to effect solvent evaporation by exposing the material under process to heat for a short duration of 1–3 seconds only. This prevents any possibility of degradation of silymarin constituents.
4. The prior art process uses methanol:water:chloroform in 1:1:1 ratio to remove undesired non-flavanolignan materials from the silymarin containing extract which gets transferred to methanol water phase. Recovery of silymarin from 50% aqueous methanol under vacuum requires long time and high input of heat energy to supply the high latent heat of vaporization of water. The process of this invention is able to achieve purification of silymarin by washing the extract with cold dichloromethane at 5° C. which having a much lower boiling point of 40.5° C. is recovered with small input of distillation heat.

In accordance with the method of invention the initial process steps are aimed at selective separation of the fatty oil from seeds of *Silybum marianum* in a single step by pre-cooling the raw materials to (−) 20° C. and carrying out the grinding of cold seeds in hammer mill fitted with 40 mesh discharge screen to obtain a powered seeds mass of optimum porosity and particle size from which it is possible to remove the total quantity of fatty oil by extraction with hexane in a soxhlet type of extractor, which is a unique feature of this invention, makes it possible to remove the total quantity of fatty oil in only 3 solvent washes, each wash having a contact time of 2.5 hours. To check for the absence of flavanolignan compounds in the hexane extract, TLC was done with a sample of hexane extract and silymarin solution (1 mg/ml in methanol), loaded on a precoated silica gel 60 mesh plate (Merck), plate run twice in the solvent system chloroform:acetone formic acid (9:2:1), developed with 1% methanolic ferric chloride solution, acidified with sulphuric acid. No reddish brown spots characteristic of flavanolignans were seen on the chromatogram of the hexane extract. Fatty oil can be recovered from the hexane extract by simple distillation and hexane recycled to the process. The defatted seed bed is freed from hexane by passing hot water at 75° C. in the jacket of the vessel holding the seed powder and a small amount of nitrogen gas is passed simultaneously through the seed powder bed to dry it completely.

The next step of this invention consists of percolation of defatted seeds with acetonitrile solvent at temperature (20° C.–30° C.) to selectively extract the flavanolignan compounds along with few impurities. Acetonitrile has been chosen as a solvent having polarity slightly higher than ethyl acetate but lower than methanol. Extraction with acetonitrile of defatted seeds at room temperature is more effective in the extraction of the flavanolignans. This step of invention avoids boiling of raw material as done with ethyl acetate in prior art processes, yet achieves higher yield of silymarin. The sensitive silymarin fraction is provided additional protection by employing a agitated wiped thin film evaporator for the concentration of the silymarin extract in acetonitrile. This type of evaporator exposes the feed material to hot water heated evaporating surface for a duration ranging from 1–3 seconds only. The non flavanoid impurities which get extracted along with silymarin are removed by stirring the dry extract twice with three times the quantity of cold dichloromethane at 5° C. Employing cold dichloromethane for this purification step minimises the loss of this volatile solvent and also minimises the loss of silymarin which is slightly soluble in cold dichloromethane. Filtered silymarin mixture is dried in a vacuum oven at 45° C. and suspended in 5 times of its weight of acetonitrile. Distilled water at room temperature, 8 to 12 times weight of silymarin is now mixed with the contents to yield a light yellow precipitate which is filtered and washed with more water. We have found that a closed vacuum buchner type filter fitted with 1–2 $\mu$m filter pad screen is quite suitable for this operation. Filtered and washed cake is pulverised in a vacuum oven tray and dried at 45° C.–50° C. at 8–10 torr absolute pressure for about 16–20 hours. Product purity is determined by DNPH method using a UV spectrophotometer at 490 nm (Wagner, V. H., Diesel, P., Saity, M., *Arzneim-Forsch*, 24(4), p 466–471, 1974). HPLC analysis of the product is performed to get more detailed information on the silymarin constituents. (Tittel, G. and Wagner, H., *Journal of Chromatography*, 153: 227–232, 1978). By following the process of this invention silymarin of 79% is obtained. The yield of silymarin based on the dry seed weight ranges between 3.4 to 4.0%.

Accordingly, the present invention provide a novel process for the isolation of silymarin from the seeds of *Silybum marianum* comprising of (i) Cooling the seeds to (–) 20° C. in a deep freezer/cold room, (ii) Powdering the cooled seeds using a hammer mill fitted with 40 mesh discharge screen, (iii) Defatting the powdered seed by extracting hexane in a soxhlet extractor to remove the total quantity of fatty oil without using a screw press, (iv) Extracting the defatted seed powder with acetonitrile at 20° C. to 30° C. to obtain silymarin fraction, (v) Concentration of sensitive silymarin fraction under vacuum in an agitated wiped thin film evaporator to obtain silymarin concentrate, (vi) Stirring the dried silymarin rich powder with cold dichloromethane at 5° C. followed by filtering and drying the purified silymarin, drying the material under nitrogen atmosphere, (vii) Further purifying silymarin by suspending with 5 times its weight of acetonitrile and precipitating with 8–12 times it weight of water at 20–30° C., (viii) Filtering the precipitated silymarin in a closed vacuum filter having 1–2 $\mu$m filter pad and washing the cake thrice with water, (ix) Drying the silymarin cake in a vacuum oven to obtain substantially pure silymarin.

In one embodiment of invention, the precooled seeds are crushed in a hammer mill fitted with 40 mesh discharge screen.

In yet another embodiment of invention, the total quantity of fatty oil in the seeds is removed in a single step by extraction with hexane in a soxhlet type extractor without the use of a screw press.

Still another another embodiment of invention, acetonitrile has been used to selectively extract the silymarin fraction from the defatted seeds.

In another embodiment of invention, extraction of silymarin has been carried out using the solvent at 20° C. to 30° C. and avoiding the use of hot solvents near their boiling point which emits toxic fumes.

EXAMPLE 1

100 gms of *Silybum marianum* seeds were kept in the deep freezer set at (–) 20° C. for 24 hours. The cold seeds were pulverised in a micro pulveriser using a 40 mesh discharge screen. The powdered material was loaded in a glass soxhlet apparatus. The powdered seed bed was sandwiched between two half inch cotton layers. 600 ml of hexane was taken in the reboiler flask and heated over a water bath to boil the solvent and start the circulation of solvent through the seed bed. Soxhlet was operated in this manner continuously for 6 hours to defatt the seeds completely. Defatted seed powder was transferred to the vacuum oven and dried at 45° C., 10 torr absolute pressure for 4 hours. Hexane extract was distilled to obtain 32.5 gm pale yellow fatty oil. The defatted dry seed powder was transferred to a 1 liter round bottom flask and macerated with 400 ml of acetonitrile at 25° C. for 3 hours. Contents were filtered in a glass buchner to separate seed material from the extract. This operation was repeated thrice by using 300 ml solvent in each of the subsequent two extractions to obtain a total quantity of 890 ml of extract. The extract was distilled in a rotary vacuum evaporator at a temperature of 50° C. to obtain a dry residue. This pale yellow residue was stirred with 15 ml of dichloromethane at 5° C. for 10 minutes, followed by filtration in a buchner with G-3 sintered disc. Another 10 ml of cold dichloromethane (5° C.) was used to wash the filter cake in the buchner. The solid material in the buchner consisting of enriched silymarin was dried in a vacuum oven (45° C., 10 torr). Dried material was suspended by stirring it with 20 ml acetonitrile at room temperature. 48 ml distilled water was added to the suspension to precipitate the silymarin. The contents were filtered in buchner and the cake was washed with 200 ml distilled water. The cake was then dried in a vacuum oven at 45° C. at 5–10 torr for 15–20 hours. Final weight of silymarin obtained: 4.21 gms; Yield based on dry seed weight: 4.2%; Purity by DNPH method: 79%.

EXAMPLE 2

The same process was carried out on pilot plant scale using 40 Kg *Silybum marianum* seeds, but using stainless steel pilot plant equipment as follows:

The seed was cooled overnight to (–) 20° C. in a deep freezer, pulverized to (–) 40 mesh in a hammer mill and charged to the drug holder of the stainless steel soxhlet pilot plant. 200 liters of hexane was pumped into the drug holder to completely immerse the powdered seeds. After a contact time of 25 hours the extract was drained into the reboiler kettle (Vol. Of Extract: 165 lt.). Steam at 10 psig line pressure was admitted into the jacket of the reboiler kettle to distill the hexane. The stem valve was regulated to maintain a flowrate of 70–80 liters/hour of condensed hexane as indicated by the flowmeter, hexane being sprayed on the seed bed surface in the drug holder. After the level of the solvent in the drug holder reached to a level of 2" above the seed bed, steam flow was stopped to allow a contact time of 2.5 hours for the second wash. The third wash was given following the same procedure as above. Fatty oil was recovered from the extract by distilling of the hexane to obtain 12.4 kg of the oil (yield of fatty oil 31%). Residual hexane from the seed bed was recovered by introducing hot water at 75° C. in the jacket of the drug holder. The complete removal of hexane from the seed bed was ensured by slow purging of dry nitrogen gas through the drug holder simultaneously for 20 minutes. 180 liter acetonitrile at 27° C. was next pumped to the drug holder to completely immerse the dry, defatted seeds. A contact time of 2.5 hours was allowed. The extract was drained and pumped to a stainless steel agitated wiped thin film evaporator through a rotameter at a flow rate of 40 liters/hour with the teflon wiper rotating at 290 rpm and hot water circulating in the evaporator jacket at 50° C. The system was maintained under vacuum of 8–10 torr by a vacuum pump. Recovered acetonitrile was used for the second and third wash Two more extractions of the defatted seed powder were carried out following the same procedure. Total volume of concentrated extract collected in the concentrate receiver of the wiped film evaporator from the three extracts was 62 liters. To achieve further enrichment of silymarin compounds in this extract, it was transferred to a batch type glass lined vacuum evaporator fitted with an anchor stirrer. Hot water at 50° C. was circulated in the jacket of the vessel and the vacuum concentrator maintained at 8–10 torr with stirrer rotation at 98 rpm. Solvent from the extract was evaporated to get a semi-solid consistency of the product. It was drained into a stainless steel tray which was immediately transferred to a vacuum oven (45° C., 8–10 torr) for complete drying. The pale yellow solid obtained from the vacuum oven was powdered and stirred with 6 liters of pre-cooled dichloromethane at 5° C. in a stainless steel stirred reactor for 5–10 minutes. Contents were transferred to a closed stainless steel vacuum filter to remove dichloromethane. The filter cake was given another wash with cold dichloromethane and dried by maintaining a slow purge of dry nitrogen gas in the cake chamber. The dry solid was stirred with 8 liters of acetonitrile at room temperature in a stainless steel reaction vessel to form a suspension. 20 liters of distilled water was added to the suspension to obtain light yellow precipitate of silymarin. The slurry was pumped to the stainless steel vacuum filter fitted with 1–2 micron screen to separate pure silymarin. The cake was washed twice with distilled water and dried in the vacuum oven at 45° C. and 5–10 torr absolute pressure for 16–20 hours. Final weight of Silymarin: 136 kg. Yield based on dry seeds: 3.4%. Purity of Silymarin by DNPH method: 77.5%. Product was stored in air tight container to prevent contact with light and air.

The present process for the isolation of Silymarin is a very economical and does not involve toxic or costly reagents. This process can be exploited on commercial scale as opposed to known processes. The present process provides pure form of silymarin which need not be subject to other purification treatment. In addition, the various solvents used can be recycled/reused in the process.

What is claimed is:

1. A process for the isolation of Silymarin, a hepatoprotective agent, from the seeds of Silybum marianum, said process comprising the steps of:
   i) chilling the seeds of Silybum marianum,
   ii) grinding the chilled seeds to a fine powder,
   iii) defatting the pulverized seeds by extracting it with a hydrocarbon solvent,
   iv) extracting the defatted seed powder with acetonitrile at 20–30° C. to obtain silymarin-containing fraction as an extract,
   v) concentration of the sensitive silymarin fraction,
   vi) stirring the silymarin rich dry powder with cold dichloromethane at 5° C. followed by filtration and drying with a slow purge of nitrogen gas,
   vii) purification of silymarin by suspending it in acetonitrile in an amount 5 times its weight and precipitating it by adding distilled water in an amount 8–12 times its weight, at 20–30° C.,
   viii) filtering the precipitated silymarin in a closed vacuum filter having 1 to 2 μm screw to form a filter cake, washing the cake three times with distilled water, and
   ix) drying the silymarin cake in vacuum oven to obtain substantially pure silymarin.

2. A process as claimed in claim 1 wherein the seeds of the plant Silybum marianum are cooled for 24 hrs. at −20° C. in a deep freezer or cold room.

3. A process as claimed in claim 1 wherein the hydrocarbon solvent for removal of fatty acids is hexane.

4. A process as claimed in claim 1 wherein the chilled seeds are pulverized in a hammer mill fitted with about 40 mesh discharge screen.

5. A process as claimed in claim 1 wherein the fatty oil in the seed powder is removed by extraction in a soxhlet type extractor without using screw/press.

6. A process as claimed in claim 1 wherein the extract containing sensitive silymarin obtained in step (iv) is concentrated using an agitated wiped thin film evaporator.

7. A process as claimed in claim 1 wherein the filtration of the silymarin containing fractions is carried out in closed vacuum filter under the inert environment of nitrogen gas to prevent the degradation of the product.

8. A process as claimed in claim 1 wherein the silymarin precipitate is dried under vacuum at 40–45° C., maintaining oven pressure at 5–15 torr for 15 hours.

9. A process for extracting of hepatoprotective agent silymarin from the seeds of Silybum marianum (L) Gaertn, said process comprising:
   a) chilling the seeds of Silybum marianum at (−)20° C. by keeping overnight in a deep freezer/cold room,
   b) grinding the chilled seeds in a hammer mill fitted with 40 mesh discharge screen,
   c) extracting the powdered seeds in a soxhlet apparatus with a hydrocarbon solvent to remove all the fatty oil,
   d) percolating the defatted seed powder 3–4 times with acetonitrile at (20° C.–30° C.) for separating the silymarin containing fraction, as extract,
   e) removing the acetonitrile under vacuum in a wiped film evaporator to obtain a concentrate rich in silymarin, recovered acetonitrile being recycled to the process,
   f) drying the concentrate in a batch type stirred vacuum concentrator to obtain a product of semi solid consistency and its further drying in a vacuum oven to obtain a dry residue,
   g) stirring the powdered residue in cold dichloromethane (5° C.) and filtering in a closed vacuum filter for removing the impurities from silymarin rich solid product,
   h) dissolving the above solid in small amount of acetonitrile and precipitating silymarin by adding cold distilled water,
   i) filtering the light yellow precipitate and washing it three times with distilled water, and
   j) transferring the cake to a vacuum oven and drying it at 40–45° C., maintaining the oven pressure at 5–15 torr for 15 hours, and thereby obtaining pure silymarin.

10. A process as claimed in claim 9 wherein the hydrocarbon solvent is hexane.

11. A process as claimed in claim 1 wherein the acetonitrile in step iv) is pure acetonitrile.

12. A process as claimed in claim 9 wherein the acetonitrile in d) is pure acetonitrile.

* * * * *